(12) United States Patent
Shimada et al.

(10) Patent No.: US 6,572,575 B1
(45) Date of Patent: Jun. 3, 2003

(54) DISPOSABLE DIAPER HAVING PATTERN SHEET, AND METHOD FOR MANUFACTURING THE SAME

(75) Inventors: Takaaki Shimada; Toru Sasaki; Hiroki Yamamoto, all of Kagawa (JP)

(73) Assignee: Uni-Charm Corporation, Ehime (JP)

( * ) Notice: Subject to any disclaimer, the term of this patent is extended or adjusted under 35 U.S.C. 154(b) by 164 days.

(21) Appl. No.: 09/641,078

(22) Filed: Aug. 17, 2000

(30) Foreign Application Priority Data

Aug. 20, 1999 (JP) .......................................... 11-233721

(51) Int. Cl.$^7$ ................................................ A61F 13/15
(52) U.S. Cl. ...................................... 602/385.01; 2/400
(58) Field of Search ................................ 602/317–402; 2/400–406

(56) References Cited

U.S. PATENT DOCUMENTS

| | | | |
|---|---|---|---|
| 4,249,532 A | 2/1981 | Polansky | 128/287 |
| 4,705,513 A | 11/1987 | Sheldon | 604/361 |
| 5,024,672 A | * 6/1991 | Widlund | |
| 5,546,607 A | * 8/1996 | Roberts | |
| 5,593,395 A | * 1/1997 | Martz | |
| 5,690,624 A | * 11/1997 | Sasaki et al. | |
| 5,809,577 A | * 9/1998 | Getz | |
| 6,307,119 B1 | * 10/2001 | Cammarota et al. | |

FOREIGN PATENT DOCUMENTS

| | | | |
|---|---|---|---|
| EP | 0554911 A1 | 8/1993 | |
| EP | 0776645 A1 | 6/1997 | |
| JP | 3090602 | 4/1991 | |
| JP | H3-58416 | 6/1991 | |
| JP | H6-86728 | 12/1994 | |
| JP | 07-313549 | 12/1995 | |
| JP | 9-140742 | 6/1997 | ........... A61F/13/42 |
| JP | 9-299401 | 11/1997 | ........... A61F/13/42 |
| JP | 10-075980 | 3/1998 | |
| JP | 10-77566 | 7/2001 | |

OTHER PUBLICATIONS

European Search Report.

* cited by examiner

Primary Examiner—Jeanette Chapman
(74) Attorney, Agent, or Firm—Darby & Darby (57) ABSTRACT

There is disclosed a disposable diaper including: an outer sheet facing outward; a liquid-permeable inner sheet facing a liquid receiving side; and an absorbent layer interposed between the outer sheet and the inner sheet, to form a front face portion to be applied to the abdomen of a wearer, an intermediate portion to be applied to the crotch, and a back face portion to be applied to the back side. A pattern sheet having a pattern and an area smaller than an area of the diaper, as viewed from the back face or the front face of the diaper, is adhered to the inner side of the outer sheet. The outer sheet allows the pattern to be observed therethrough.

11 Claims, 5 Drawing Sheets

DISPOSABLE DIAPER HAVING PATTERN SHEET, AND METHOD FOR MANUFACTURING THE SAME

BACKGROUND OF THE INVENTION

1. Field of the Invention

The present invention relates to a disposable diaper and further to a disposable diaper having a pattern sheet allowing a pattern printed thereon to be observed only at a portion of the back face or front face of the diaper, and a method for manufacturing the same.

2. Description of the Related Art

In either the so-called "open type" disposable diaper for infants or babies or a disposable diaper which is formed in advance into the underpants shape, it is customary that a pattern such as the image of an animal or character appears on the outer sheet of the diaper.

The conventional method for attaching the pattern is generally done by printing a film to form the outer sheet (or back sheet) of the diaper in advance with continuous patterns or repeated patterns and by manufacturing the diapers of the outer sheet continuously by an automatic machine.

In the disclosure of Japanese Patent Laid-Open No. H3-90602 (90602/1991), on the other hand, a see-through outer sheet (or back sheet) is used and is jointed to another member on the inner side through a hot-melt type adhesive having a color. This hot-melt type adhesive is applied in a dotted shape to form a highly dense region of dots for expressing such an image or pattern as can be observed through the outer sheet.

The aforementioned method for manufacturing the diaper by using the film printed in advance with the pattern as the outer sheet is accompanied by the step of laying an absorbent layer and a liquid-permeable inner sheet (or top sheet) over the outer sheet having a band shape and by the subsequent step of separating individual diapers. This makes it substantially impossible for the completed disposable diaper to control what of its surface position the pattern or image is located at. It follows that the print on the outer sheet is limited to the continuous patterns or the repeated patterns, as described above, to restrict the degree of freedom for selecting the design of the pattern to appear on the surface. On the other hand, it is necessary to print the entire film for the outer sheet. This necessity raises the cost for manufacturing the outer sheet (or a film having the printed pattern). This cost is extremely raised if the pattern is to be expressed by the multicolor print, for example.

In the disclosure of Japanese Patent Laid-Open No. H3-90602 (90602/1991), moreover, a colored hot-melt type adhesive is applied to the outer sheet by using a roll coater to express the pattern by the dot application. This expression is unable not only to achieve a clear pattern but also to make a multicolor pattern. Moreover, although FIG. 1 of Japanese Patent Laid-Open No. H3-90602 (90602/1991) shows the pattern appearing only on one portion of the diaper, there arises a defect that a dislocation is liable to occur between the completed diaper and the pattern if the pattern is attached by the roll coater according to the aforementioned method.

SUMMARY OF THE INVENTION

The present invention has an object to provide a disposable diaper capable of attaching a pattern to only one portion of the diaper at a low cost and preventing any serious cost rise even where the pattern of a multicolor print is used, for example, and a method for manufacturing the disposable diaper.

According to the invention, there is provided a disposable diaper, comprising: an outer sheet facing outward; a liquid-permeable inner sheet facing a liquid receiving side; and an absorbent layer interposed between the outer sheet and the inner sheet, to form a front face portion to be applied to the abdomen of a wearer, an intermediate portion to be applied to the crotch, and a back face portion to be applied to the back side, wherein a pattern sheet having a pattern and an area smaller than an area of the diaper, as viewed from the back face or the front face of the diaper, is adhered to the inner side of the outer sheet; and wherein the outer sheet allows the pattern to be observed therethrough.

The disposable diaper of the invention may be the so-called "open type" or may be formed in advance into an underpants type.

The view of the disposable diaper, as taken from the back face or the front face, means that the diaper is flattened, while not being worn by a human body, to have its front face portion and back face portion in face-to-face contact with each other, and that this state is seen from the back side or the front side. Alternatively, the view means the projected shape taken from the back face or the front face by making the disposable diaper the same stereoscopic as it is worn by the human body. In short, it is sufficient to satisfy that the area to be occupied by the pattern sheet is smaller than the area (or the projected area) of the diaper either in the flattened state or in the stereoscopic state.

For example, it is preferred that the area to be occupied by the pattern sheet is 50% or less of the area of the diaper, as viewed from the back face or the front face of the diaper.

The pattern sheet may have any of polygonal, circular and elliptical shapes.

Preferably, the pattern sheet is an air- and moisture-permeable sheet on the surface of which the pattern is printed.

When the pattern sheet is exemplified by the air- and moisture-permeable sheet, as specified above, and when the outer sheet is also air- and moisture-permeable, the air- and moisture-permeating functions of the outer sheet are not obstructed by the pattern sheet adhered thereto. When the pattern sheet is so small as to have 50% or less of the area of the outer sheet, as viewed from the back face or the front face of the diaper, however, those functions of the outer sheet are hardly influenced and the entire diaper is prevented from being steamed stuffy, even if the pattern sheet has no air -and moisture-permeability.

For example: the outer sheet may be made of a nonwoven fabric; a liquid-impermeable sheet or a hydrophobic sheet may be disposed inside of the outer sheet; and the pattern sheet may be adhered between the outer sheet and the liquid-impermeable sheet or the hydrophobic sheet.

Alternatively, the outer sheet may be made of a film, and the pattern sheet may be adhered to the inner face of the film.

According to the invention, on the other hand, there is provided a method for manufacturing a disposable diaper, comprising: an outer sheet facing outward; a liquid-permeable inner sheet facing a liquid receiving side; and an absorbent layer interposed between the outer sheet and the inner sheet, to form a front face portion to be applied to the abdomen of a wearer, an intermediate portion to be applied to the crotch, and a back face portion to be applied to the back side, the method comprising:

(a) the step of adhering a pattern sheet having a pattern and a smaller area than an outer sheet to a predetermined position on the inner face of the outer sheet which can be seen through;

(b) the step of placing an absorbent layer on the inner side of the outer sheet; and (c) the step of laminating an inner sheet on the inner side of the absorbent layer, so that the pattern of the pattern sheet having an area smaller than an area of the diaper, as viewed from the back face or the front face of the diaper, can be seen through the outer sheet.

In this case, between the step (a) and the step (b), there can be further comprised the step of laying a liquid-impermeable sheet or a hydrophobic sheet for covering the inner side of the outer sheet, and sandwiching the pattern sheet between the outer sheet and the liquid-impermeable sheet or the hydrophobic sheet.

If the precision at the time of adhering the pattern sheet to the outer sheet is retained, according to the manufacture method of the invention, the pattern can be attached to the predetermined position of the diaper without dislocation. It is also possible to easily match the changes in the position and the size of the pattern.

DESCRIPTION OF THE PREFERRED EMBODIMENT

Figure 1:
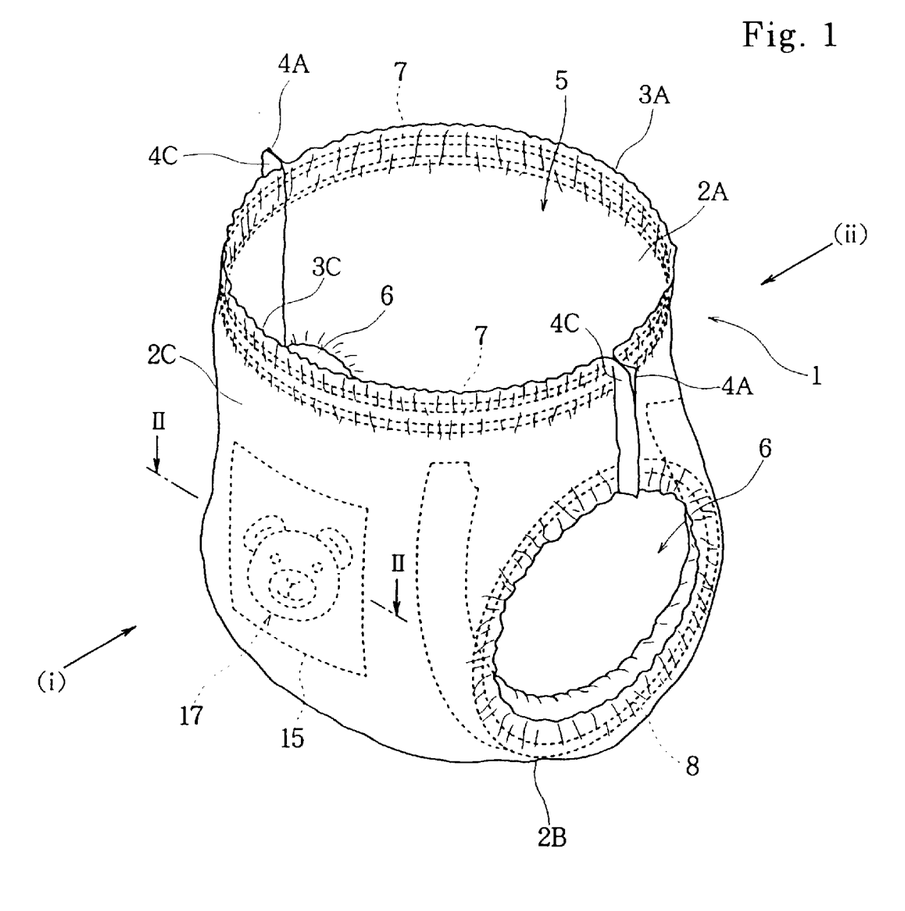
FIG. 1 is a perspective view showing an underpants type diaper according to one embodiment of the invention.
Figure 2:
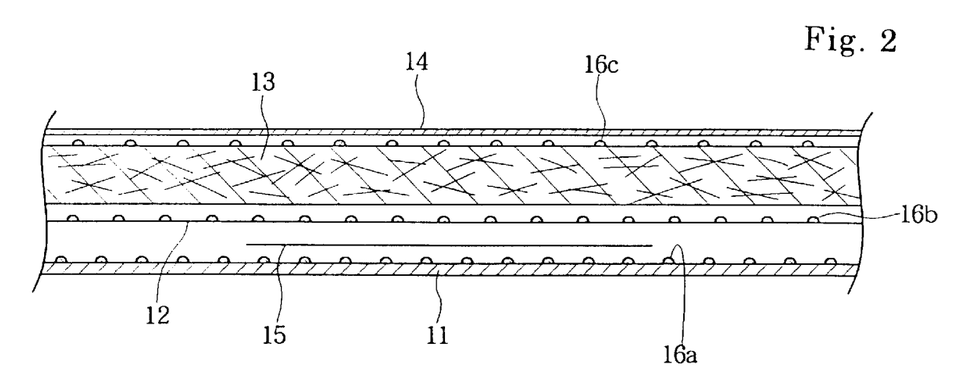
FIG. 2 is a section of the underpants type disposable diaper shown in FIG. 1 taken along line II—II.
Figure 5:
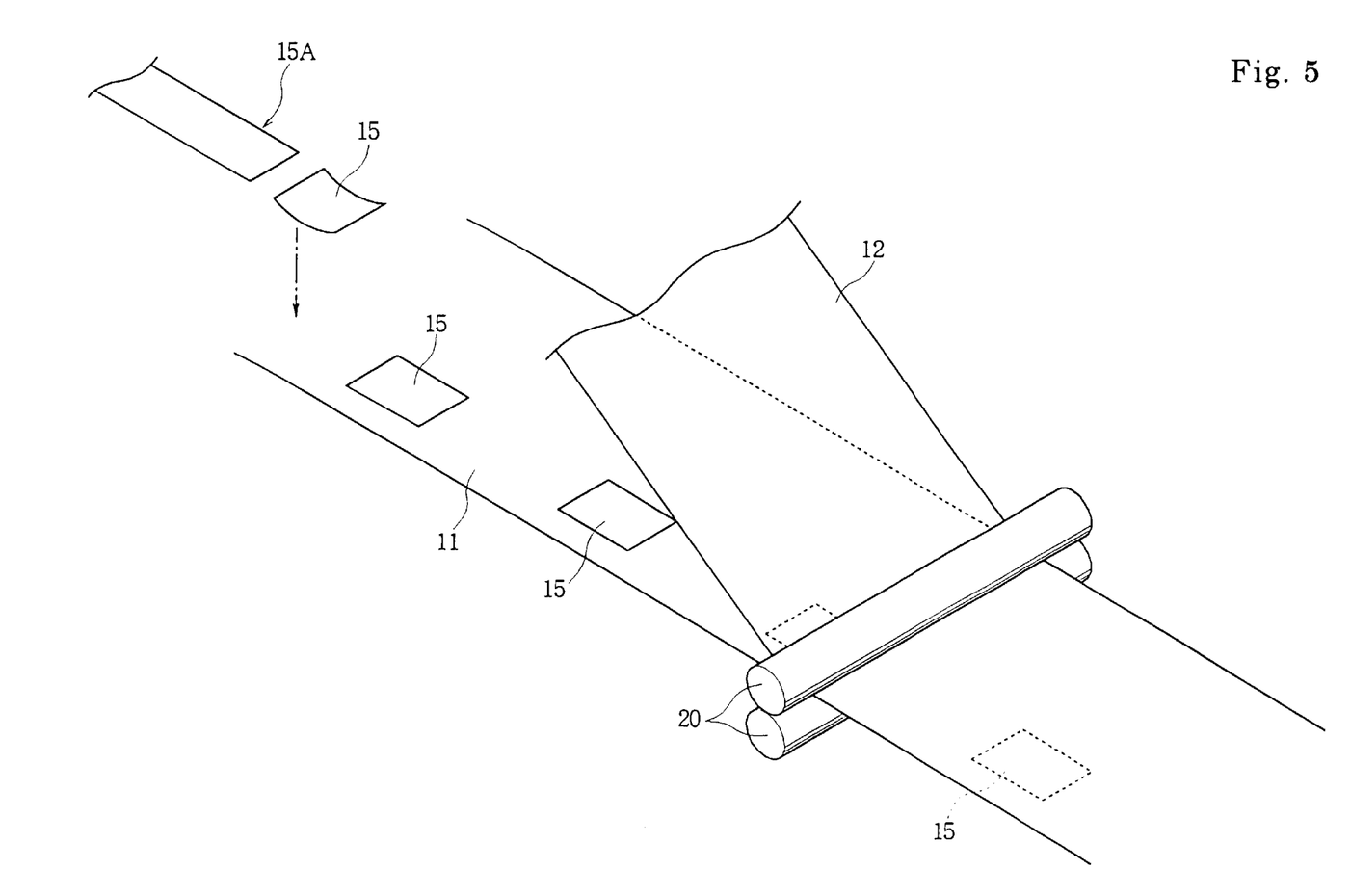
FIG. 5 is a perspective view showing a method for manufacturing the disposable diaper of FIG. 1.
Figure 6:
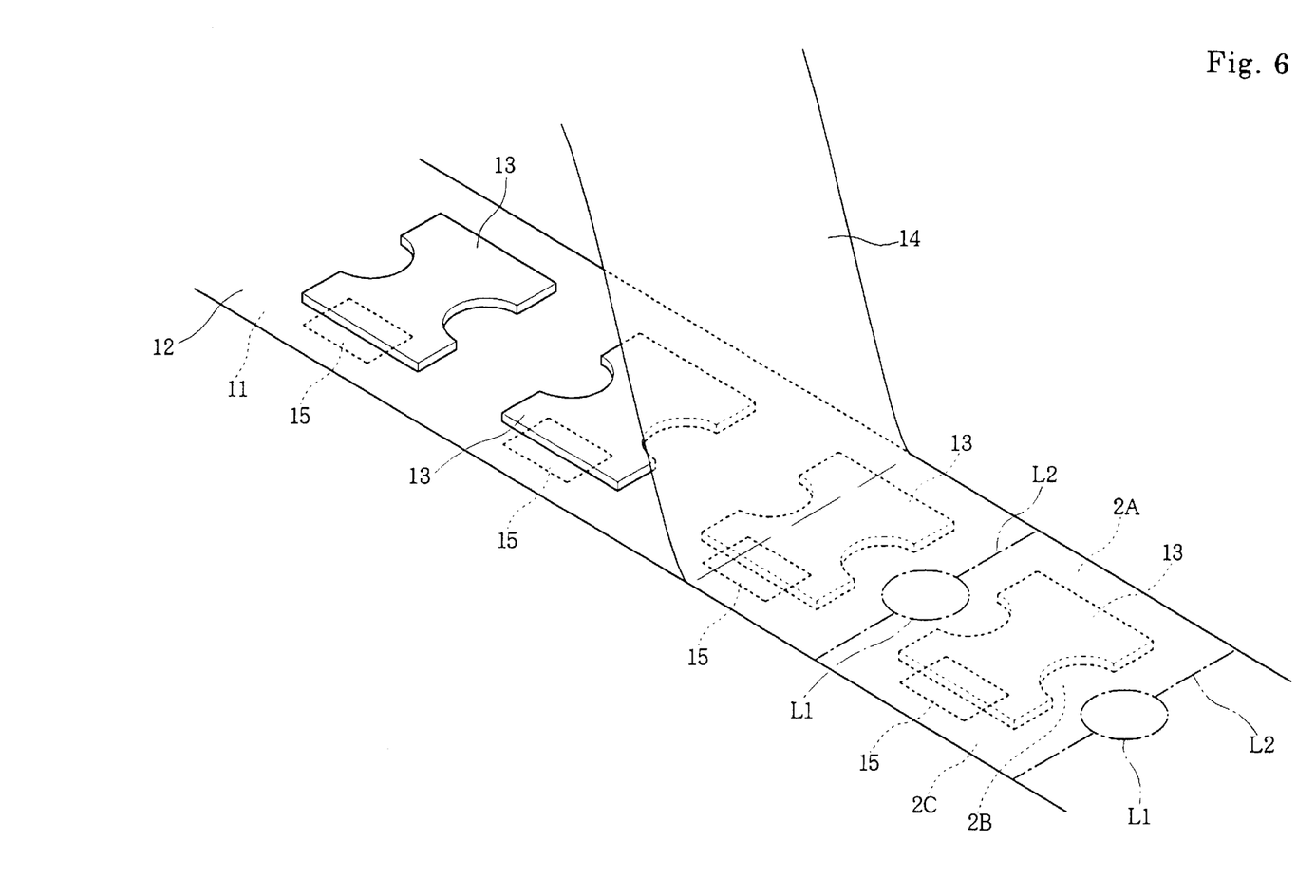
FIG. 6 is a perspective view showing a method for manufacturing the disposable diaper of FIG. 1.

FIG. 1 is a perspective view showing a disposable diaper of underpants type according to one embodiment of the invention; FIG. 2 is a section of the underpants type disposable diaper shown in FIG. 1 taken along line II—II; and FIGS. 5 and 6 are perspective views showing one example of a method for manufacturing the disposable diaper.

A disposable diaper 1 according to one embodiment of the invention, as shown in FIG. 1, is formed in advance into a underpants shape, and has the so-called "hourglass shape" in the extended state before formed. This diaper 1 has: a front face portion 2A to be applied for use to the abdomen of a wearer; a back face portion 2C to be applied for use to the buttock and/or back; and an intermediate portion 2B to be applied for use to the crotch.

The transverse side portions 4A of the front face portion 2A and the transverse side portions 4C of the back face portion 2C are jointed to each other. As a result,the waist end portion 3A of the front face portion 2A and the waist end portion 3C of the back face portion 2C form a waist opening 5. Moreover, leg openings 6 are so formed on the left and right hands as to extend in the front face portion 2A, the intermediate portions 2B and the back face portion 2C.

Elastic members (or elastic bands) 7 are transversely attached to the waist end portions 3A and 3C so that a waist gather is formed along the waist opening 5 by the elastically shrinking forces of the elastic members 7, as shown in FIG. 1. Elastic members (or elastic bands) 8 are attached around the leg openings 6 so that leg gathers (or cuffs on the leg sides) are formed around the leg openings 6 by the elastic shrinking forces of the elastic members 8, as shown in FIG. 1.

In the section of FIG. 2, the lower side presents the outer side of the diaper 1, and the upper side presents the inner side of the diaper 1. In this laminated structure of the diaper, over the inner side of an outer sheet 11 made of a nonwoven fabric or an air- and moisture-permeable material, there is laid a waterproof sheet 12 (or liquid-impermeable sheet) which is made of an air- and moisture-permeable film. Over the inner side of the waterproof sheet 12, there is laid an absorbent layer 13, over which there is laid a liquid-permeable inner sheet 14 on the innermost side. Between the outer sheet 11 and the waterproof sheet 12, there is sandwiched a pattern sheet 15 having a square shape.

To the inner face of the outer sheet 11, there is applied a hot-melt type adhesive 16a randomly, for example in an undulating shape. This hot-melt type adhesive 16a adheres the outer sheet 11 and the waterproof sheet 12. By this hot-melt type adhesive 16a, also, the pattern sheet 15 is adhered and fixed to the outer sheet 11.

To the inner face of the waterproof sheet 12 and the inner face of the absorbent layer 13, on the other hand, there are also randomly applied hot-melt type adhesives 16b and 16c to adhere the waterproof sheet 12 and the absorbent layer 13 and adhere the absorbent layer 13 and the inner sheet 14.

The outer sheet 11, the inner sheet 14 and the waterproof sheet 12 take the common hourglass shape as a whole when the diaper 1 is extended. However, the waterproof sheet 12 may exclusively have a smaller shape than that of the outer sheet 11 and the inner sheet 14. On the other hand, the absorbent layer 13 has an hourglass shape slightly smaller than that of the outer sheet 11 and the inner sheet 14. Moreover, the outer sheet 11 and the inner sheet 14 (and the waterproof sheet 12) are adhered to each other by the hot-melt type adhesives 16a and 16b at their positions apart from the periphery of the absorbent layer 13, that is, at the transverse side portions 4A of the front face portion 2A, at the transverse side portions 4C of the back face portion 2C, at the waist end portions 3A and 3C and at the peripheries of the waist openings 5.

On the other hand, the pattern sheet 15 takes a sufficiently smaller area than that of the outer sheet 11 and is printed on its outer face side with a pattern 17 such as an illustration of an animal's face, a character or a plant, a symbol or a letter. In the shown embodiment, one pattern sheet 15 is printed with a one-point pattern 17. On the other hand, any combination of the illustration, the symbol or the letter may be printed as the pattern 17. The pattern sheet 15 has the small square shape so that the blank around the pattern 17 has a small area. This makes it possible to form the pattern sheet 15 at a low cost. On the other hand, the pattern sheet 15 and the pattern 17 itself are small in size so that a drastic rise in the cost can be suppressed even if the pattern 17 is printed in multiple colors.

The pattern sheet 15 may be made of any materials which can be clearly printed with the pattern 17, for example, a resin film of polyethylene or polypropylene, paper, or a laminate of paper and a resin film. When the pattern sheet 15 is made of a resin film, however, the resin film is preferably air- and moisture-permeable so as to prevent the deterioration of the air- and moisture-permeabilities at the portion to which the pattern sheet 15 is attached. On the other hand, the pattern sheet 15 may be made of point-bonded, spun-bonded or spun-lace nonwoven fabric. The pattern sheet 15 made of this nonwoven fabric is air- and moisture-permeable.

The outer sheet 11 may be made of nonwoven fabric having such an optical transmissivity that the pattern 17 can be visually confirmed therethrough, for example, point-bonded, air-through, spun-bonded or spun-lace nonwoven fabric.

The waterproof sheet 12 may be made of an air- and moisture-permeable resin film of polyethylene or polypropylene. The absorbent layer 13 may be made of any absorbent materials. For example, the absorbent layer 13 is formed by wrapping pulverized pulp or a mixture of pulverized pulp and a highly water absorbing polymer, with an absorbent sheet such as tissue paper or the like.

The inner sheet 14 is liquid-permeable and may be made of any materials such as hydrophobic fibers subjected to a hydrophilic treatment, hydrophilic fibers or the like, as exemplified by a point-bonded, air-through, spun-bonded or spun-lace nonwoven fabric. Alternatively, the inner sheet 14 may be formed by laying a cushion layer of a bulky nonwoven fabric over the aforementioned nonwoven fabric.

The pattern sheet 15 may be attached either to the back face portion 2C of the diaper 1 or to a region from the back face portion 2C to the intermediate portion 2B. In this case, as viewed from the back face (or in the direction (i)) where the disposable diaper 1 is either in the stereoscopic state (in the same state as it is worn by a human body) as shown in FIG. 1 or in the flattened state with the front face portion 2A and the back face portion 2C in face-to-face contact with each other, the area to be occupied by the pattern sheet 15 is so small with respect to the observed entire area of the diaper that the area of the pattern sheet 15 is preferably 50% or less of the observed entire area.

On the other hand, the pattern sheet 15 may be attached either to the front face portion 2A of the diaper 1 or to a region from the front face portion 2A to the intermediate portion 2B. In this case, as viewed from the front face (or in the direction (ii)) in the stereoscopic state or in the flattened state of the diaper 1, the area to be occupied by the pattern sheet 15 is so small with respect to the observed entire area of the diaper that the area of the pattern sheet 15 is preferably 50% or less of the observed entire area.

The pattern sheet 15 may be attached to both the front face portion 2A and the back face portion 2C.

The pattern sheet 15 can be attached to an arbitrary position but is preferred to keep away from both the waist gather, as made of the elastic members 7, around the waist opening 5 and the leg gathers, as made of the elastic members 8, around the leg openings 6. Moreover, if the diaper is formed with an additional gather extending continuously around the trunk from the front face portion 2A to the back face portion 2C, the pattern sheet 15 is also preferred to keep away from the region of the gather.

When the pattern sheet 15 is attached to keep away from the aforementioned gathers, the pattern sheet 15 can keep the relatively flat state to prevent the pattern 17 from being distorted.

Moreover, the pattern sheet 15 is preferred to keep away from the joint portions between the transverse side portions 4A of the front face portion 2A and the transverse side portions 4C of the back face portion 2C. These joints of the side portions 4A and 4C are made by thermally fusing them but are troubled if the pattern sheet 15 is present therein.

Here will be described a method for manufacturing the disposable diaper 1 shown in FIGS. 1 and 2.

The hot-melt type adhesive 16a is applied to a nonwoven fabric to form the outer sheet 11, and the pattern sheets 15, as printed in advance with the pattern 17, are then positioned at a constant interval and placed on the nonwoven fabric, as shown in FIG. 5. The pattern sheets 15 are cut out at a predetermined size from a band-shaped sheet (or tape-shaped sheet) 15A. These individual pattern sheets 15 are cut away at the interval to present the homogeneous patterns 17 and are sequentially placed on the nonwoven fabric.

A film to form the waterproof sheet 12 is laid over the outer sheet 11 and is held between and given a heat by heating rollers 20 so that the individual pattern sheets 15 are sandwiched and adhered between the nonwoven fabric to form the outer sheet 11 and the film to form the waterproof sheet 12.

Next, the hot-melt type adhesive 16b is applied to the upper face of the film i.e., to the upper face of the jointed body composed of the nonwoven fabric to form the outer sheet 11 and the film to form the waterproof sheet 12. As shown in FIG. 6, then, the absorbent layers 13 are so placed at the interval on the jointed body as to match the relative positions of the pattern sheets 15. On the other hand, the hot-melt type adhesive 16c is applied to the surface of the absorbent layers 13.

And, another nonwoven fabric to form the inner sheet 14 is laid over the absorbent layers 13 to obtain a laminate, and this laminate is held between heating rollers so that its individual components are adhered to each other. After this, the laminate is cut along a cutting line L1 (to form the leg openings when the underpants shape is completed), and then is divided along a cutting line L2 into individual laminates each including the front face portion 2A, the back face portion 2C and the intermediate portion 2B. Moreover, the transverse side portions 4A of the front face portion 2A and the transverse side portion 4C of the back face portion 2C are jointed to each other to form the underpants shape, as shown in FIG. 1.

Here, from the process thus far described, there is omitted the steps of attaching the elastic members 7 and the elastic members 8.

Figure 3:
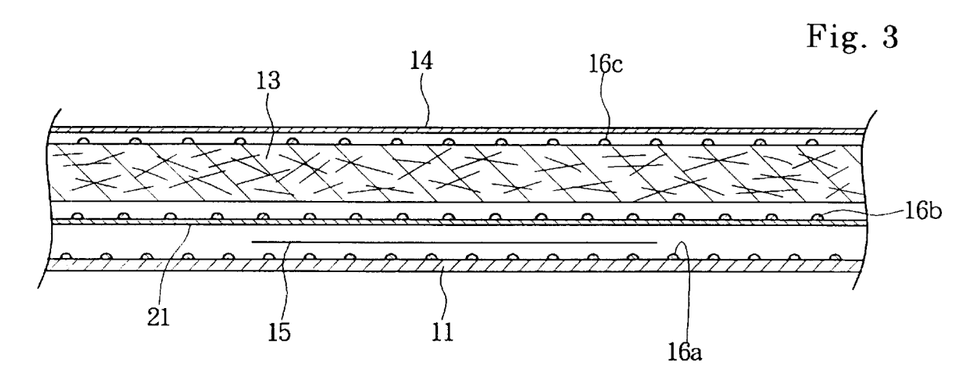
FIG. 3 is a section showing another embodiment of a laminated structure.
Figure 4:
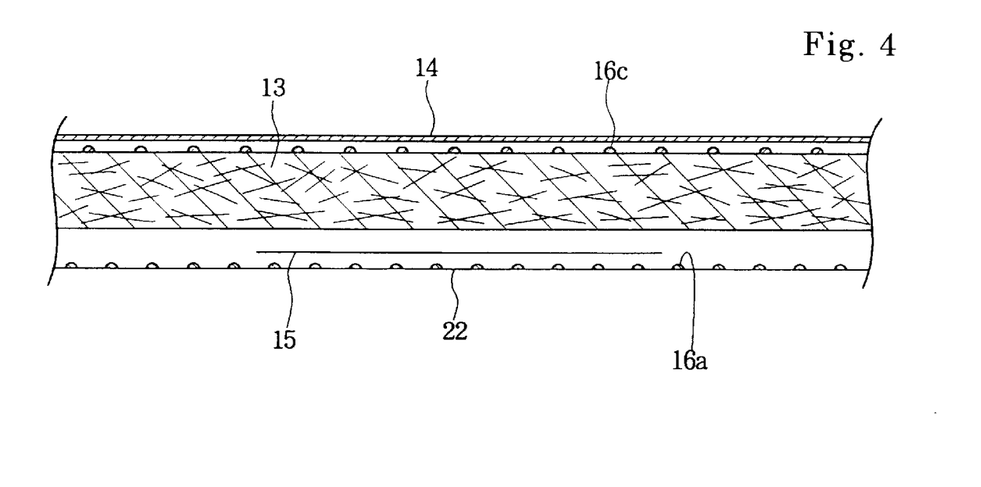
FIG. 4 is a section showing still another embodiment of the laminated structure.

FIGS. 3 and 4 are sections showing other embodiments of the structure of the laminate to form the disposable diaper 1.

In the structure shown in FIG. 3, on the inner side of the outer sheet 11, there is laid a nonwoven fabric 21 which is a hydrophobic sheet having air- and moisture-permeabilities. Between these nonwoven fabric 21 and outer sheet 11, there is sandwiched and adhered the pattern sheet 15. The nonwoven fabric 21 is exemplified by a spun-bonded nonwoven fabric made of polypropylene fibers, a sheet prepared by overlaying a spun-bonded nonwoven fabric, a melt-blown nonwoven fabric and a spun-bonded nonwoven fabric, or the like.

In the structure shown in FIG. 4, there is employed an outer sheet 22 made of a waterproof film. This waterproof film is exemplified by a resin film of polyethylene or polypropylene having air- and moisture-permeabilities. This waterproof film is made transparent or semitransparent and has such an optical transmissivity as to allow the pattern 17 of the pattern sheet 15 to be seen therethrough. The hot-melt type adhesive 16a is applied to the inner face of the outer sheet 22 made of the waterproof film, and the pattern sheet 15 is adhered over that inner face. The absorbent layer 13 is located on the inner side of the pattern sheet 15.

Figure 7A:
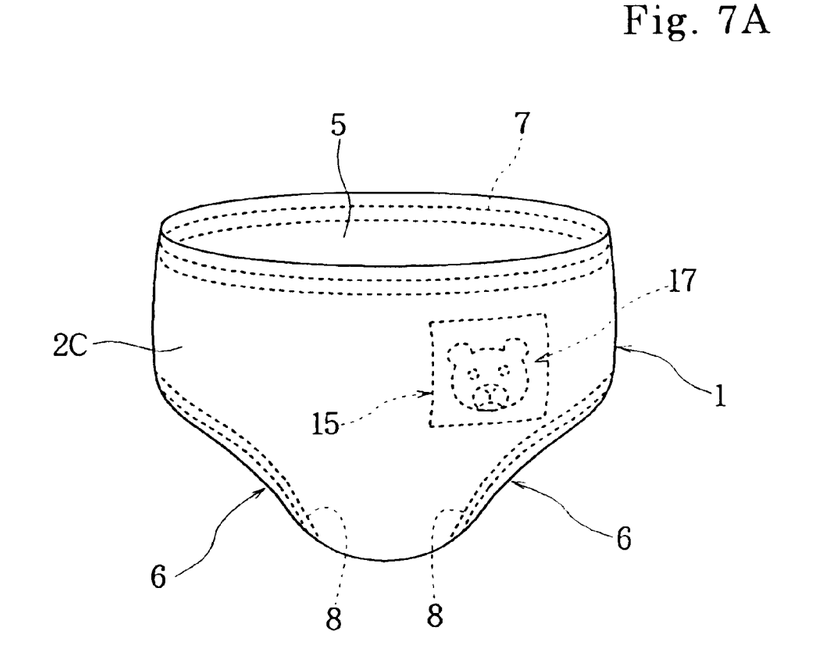
FIGS. 7A and 7B are back elevations showing modifications of the location at which a pattern and patterns are attached to the diaper.
Figure 7B:
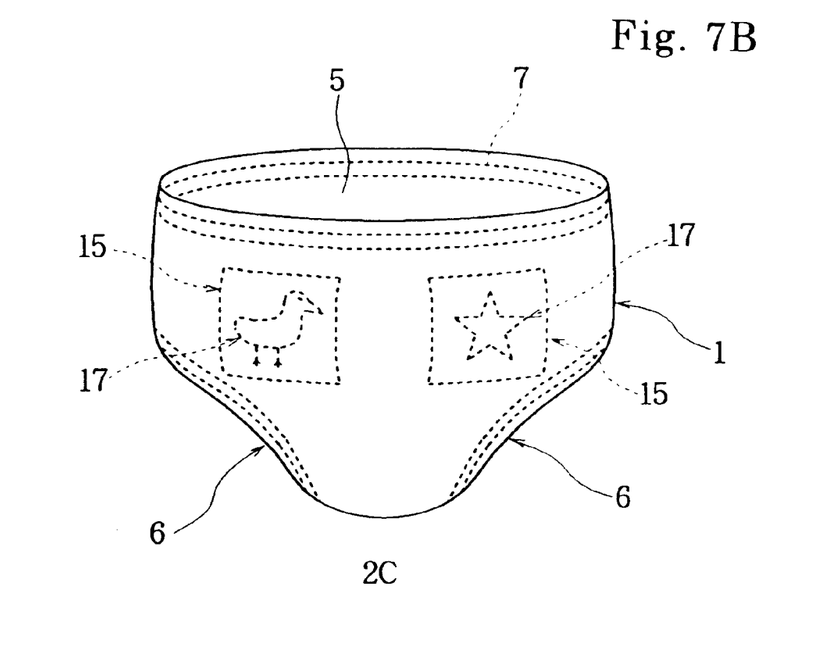

Next, FIGS. 7A and 7B are back elevations showing modifications of the mounting positions of the pattern sheet 15.

In the modification shown in FIG. 7A, the pattern sheet 15 is located on the back face portion 2C of the disposable diaper 1 at a position which is offset rightward and well balanced in its entirety. In the modification shown in FIG. 7B, the two pattern sheets 15 printed with different patterns are located on the back face portion 2C at positions which are well balanced on the left and right sides.

Thus, in the invention, the pattern 17 can be attached at an arbitrary position of the diaper 1 and in an arbitrary number so that the degree for freedom for its design is enhanced.

On the other hand, the pattern sheet 15 should not be limited to the square or rectangular shape but may be exemplified by a polygonal shape such as a triangular or pentagonal shape, a circular shape and an elliptical shape.

Here, the disposable diaper of the invention should not be limited to the underpants type shown in FIG. 1 but may be the so-called "open type" such as the hourglass type. As a result of the various structures described in detail above, advantages of the invention may include one or more of the following:

(a) The pattern can be attached to an arbitrary position.
(b) The pattern sheet used has a relatively small area to spare the sheet material such as the resin film for forming the pattern sheet.
(c) The pattern is printed on the pattern sheet of the small area so that the cost for printing it, particularly for printing it in multiple colors, can be made lower than that of the prior art for printing the whole outer sheet with the continuous patterns or repeated patterns.
(d) The pattern in an arbitrary number can be positioned highly precisely on the diaper with little dislocation.
(e) The manufacture method can easily match the change in the pattern to be applied to the diaper or the change in the location of the pattern.

Here, 'comprises/comprising' when used in this specification is taken to specify the presence of stat ed features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. A disposable diaper, comprising:
an outer sheet facing outward; a liquid-permeable inner sheet facing a liquid receiving side; and
an absorbent layer interposed between the outer sheet and the inner sheet, to form a front face portion to be applied to the abdomen of a wearer, an intermediate portion to be applied to the crotch, and a back face portion to be applied to the back side,
wherein a pattern sheet which is made of an air- and moisture-permeable resin film, is adhered with an adhesive to the inner face of the outer sheet, which is made of an air- and moisture-permeable nonwoven fabric, the pattern sheet occupies less than 50% of the area of the diaper, as viewed from the back face or the front face of the diaper, and the pattern sheet has a pattern of multiple colors printed on the face directed to the outer sheet so that the pattern is visually recognizable through the outer sheet.

2. A disposable diaper having a pattern sheet as set forth in claim 1, wherein the pattern sheet has any of polygonal, circular and elliptical shapes.

3. A disposable diaper having a pattern sheet as set forth in claim 1, wherein an air- and moisture-permeable but liquid-impermeable sheet is disposed inside of the outer sheet, and wherein the pattern sheet is disposed between the outer sheet and the liquid-impermeable sheet.

4. A disposable diaper having a pattern sheet as set forth in claim 1, wherein the adhesive is a hot-melt type adhesive randomly applied to the inner face of the outer sheet.

5. A disposable diaper having a pattern sheet as set forth in claim 1, wherein the diaper is an underpants type diaper in which side portions of the front face portion are respectively joined to corresponding side portions of the back face portion such that a waist opening and two leg openings are formed, wherein elastic members are provided around the waist opening and the two leg openings such that a waist gather and two leg gathers are provided, and wherein the pattern sheet is positioned so as to be kept away from both the waist gather and the two leg gathers.

6. A disposable diaper having a pattern sheet as set forth in claim 5, wherein an additional gather is provided to extend continuously around the trunk of the underpants type diaper from the front face portion to the back face portion, wherein the pattern sheet is positioned so as to be kept away from the trunk gather.

7. A method for manufacturing a disposable diaper having a front face portion to be applied to the abdomen of a wearer, an intermediate portion to be applied to the crotch, and a back face portion to be applied to the back side, the method comprising:

(a) the step of adhering a pattern sheet, which is made of an air- and moisture-permeable resin film and has a pattern of multiple colors printed thereon, to a predetermined position on one face of an outer sheet, which is made of an air- and moisture-permeable nonwoven fabric and has a larger area than the area of the pattern sheet, the adhering of the pattern sheet being performed with an adhesive while directing the printed pattern toward the outer sheet to make the printed pattern visually recognizable through the outer sheet, and (b) stacking an absorbent layer and a liquid-permeable inner sheet on the face of the outer sheet to which the pattern sheet is adhered, so that in the resulting diaper, the absorbent layer is interposed between the outer sheet and the inner sheet, and the pattern sheet occupies less than 50% of the area of the diaper as viewed from the back face or the front face of the diaper.

8. The method as set forth in claim 7, wherein the adhesive is a hot-melt type adhesive and randomly applied to the outer sheet.

9. The method as set forth in claim 7, wherein the diaper is of underpants type in which side portions of the front face portion are joined to respective corresponding side portions of the back face portion such that a waist opening and two leg openings are formed, and wherein elastic members are respectively provided around the waist opening and the two leg openings such that a waist gather and two leg gathers are provided, wherein the pattern sheet is positioned so as to be kept away from both the waist gather and the two leg gathers.

10. The method as set forth in claim 9, wherein an additional gather is provided to extend continuously around the trunk of the underpants type diaper from the front face portion to the back face portion, wherein the pattern sheet is positioned so as to be kept away from the trunk gather.

11. The method as set forth in claim 7, further comprising, between the step (a) and the step (b), the step of laying an air- and moisture-permeable but liquid-impermeable sheet on the outer sheet to sandwich the pattern sheet between the outer sheet and the liquid-impermeable sheet.

* * * * *